United States Patent
Galantai

(10) Patent No.: US 6,889,402 B2
(45) Date of Patent: May 10, 2005

(54) PULL THROUGHS

(75) Inventor: Roderick Francis Galantai, Auckland (NZ)

(73) Assignee: Galantai (Plastics) Group Limited, Auckland (NZ)

( * ) Notice: Subject to any disclaimer, the term of this patent is extended or adjusted under 35 U.S.C. 154(b) by 288 days.

(21) Appl. No.: 10/124,728

(22) Filed: Apr. 18, 2002

(65) Prior Publication Data

US 2002/0157200 A1 Oct. 31, 2002

Related U.S. Application Data

(63) Continuation of application No. PCT/NZ00/00198, filed on Oct. 12, 2000.
(51) Int. Cl.⁷ .............................. B08B 9/04; B29C 45/14
(52) U.S. Cl. ............................... 15/104.05; 15/104.16; 264/265
(58) Field of Search ........................ 15/104.05, 104.16, 15/104.165; 42/95

(56) References Cited

U.S. PATENT DOCUMENTS 3,205,518 A * 9/1965 Romaine ............... 15/104.165
4,873,778 A * 10/1989 Stipp .............................. 42/95
4,962,607 A * 10/1990 Baldwin ......................... 42/95
5,171,925 A * 12/1992 Mekler .......................... 42/95
5,555,588 A * 9/1996 Viesehon ................. 15/104.16
5,651,207 A * 7/1997 Knight .......................... 42/95
5,972,125 A * 10/1999 Hedge ......................... 134/8
6,088,866 A * 7/2000 Hedge ..................... 15/104.16

FOREIGN PATENT DOCUMENTS

| AU | 741733 | 4/1998 |
| JP | 8-173379 | 7/1996 |
| WO | WO00/10476 | 3/2000 |

* cited by examiner

*Primary Examiner*—Randall Chin
(74) *Attorney, Agent, or Firm*—Jacobson Holman PLLC

(57) ABSTRACT

A pull through such as might be used for an endoscope where a thermaplastics monofilament substantially free of spool or coil memory has molded thereon a desirable thermoplastic mass profile in a material of lower melting point than at least part of the filament, such melting point differential with preferably pre-heating of the filament ensuring an appropriate keying of the profile on the filament.

27 Claims, 2 Drawing Sheets

PULL THROUGHS

This is a continuation of PCT/NZ00/00198, filed Oct. 12, 2000 and published in English.

FIELD OF THE INVENTION

The present invention relates to a pull through and related methods of manufacture, use and dispensing. In one form such a pull through is a pull through for an endoscopic and a method for manufacturing such apparatus.

Endoscopes require frequent cleaning. It is found that endoscopes (such as those lined with, for example, a polyurethane sleeve) are perhaps best sterilised between uses by a cleaning regime that involves the pushing and/or pulling through of a brush the effect of which is to smooth the inwardly directed surface and surface deposits of the polyurethane sleeve or its equivalent. Apparently this better enables chemical cleaning and sterilisation to ensue. See for example the post Mar. 2, 2000 published content of PCT/AU99/00669 (WO 00/10476) of Novapharm Research (Australia) Pty Limited the full content of which is here included by way of reference.

SUMMARY OF THE INVENTION

The present invention is directed to any such pull through apparatus, all uses of such apparatus and methods for manufacturing such apparatus.

As used herein the term "pull through" also includes (where the circumstance allows) a "push through" device. Frequently, by way of example, where a short length conduit is to be dealt with, it is sometimes just as convenient to push the head of a pull through type device through the device rather than thread and then pull the pull through device through the short length conduit. Accordingly the term "pull through" in the present specification and in the appended claims includes within its ambit any variant capable in some circumstances of being used as a push through.

In a first aspect the invention is a pull through comprising or including a filament having at least a thermoplastics surface, and a moulded thermoplastic mass about said filament defining a pull through profile adapted for the purpose of the pull through, wherein the filament is a monofilament (whether of the one material or otherwise) sufficiently stiff to enable its threading through the member (e.g. endoscope, fuel line, conduit, barrel, etc.) for which it is adapted or intended for use, and wherein said moulded thermoplastic mass is of a material of lower melting point than at least part of said filament.

Preferably said monofilament is of a single plastics material.

Preferably said single plastics material is polypropylene.

Preferably the moulded thermoplastics mass is of polyethylene (eg; LLDPE) and a polyolefin elastomer. Examples include SANTOPRENE™, DOWLEX™ and ENGAGE™.

Preferably said filament is round in section.

Preferably said moulded thermoplastics mass is adjacent one end of said filament.

Preferably said moulded thermoplastics mass has been injection moulded about said filament only once the thermoplastics surface of said filament onto which it is to be injection moulded has been softened and/or conditioned.

Preferably said filament is substantially straight and free of any previous spool or coil memory.

Preferably said filament is conditioned by heating prior to said mass being injection moulded.

Preferably said filament is conditioned by heating and stretching prior to said mass being injection moulded.

Preferably said filament is a monofilament of polypropylene that has been heated preferably to from 91 to 95° C. (e.g. 93 to 95° C.) for preferably from 8 to 15 seconds (e.g. about 12 seconds) whilst preferably being stretched axially preferably by from 1 to 5% of its length from a feeder spool or coil.

Preferably said polypropylene monofilament has been extruded whilst including a gas generating agent which will expand the core region thereof upon die emergence.

Preferably said gas generating agent releases $CO_2$.

Preferably said gas generating agent inclusion is such as to enhance the circularity of cross-section of the monofilament from the extrusion die.

Preferably said mass is of a profile (which whilst it may differ axially with respect to the filament) is laterally preferably symmetric about said filament.

In another aspect the invention is an endoscope pull through, being a pull through as previously defined.

In yet another aspect the invention is a conduit pull through, being a pull through as previously defined.

In another aspect the invention is a method of manufacturing a pull through, said pull through comprising or including a filament having at least a thermoplastics surface, and a moulded thermoplastic mass about said filament defining a pull through profile adapted for the purpose of the pull through, said method comprising or including providing a coil or spool feeding of a monofilament filament having at least a thermoplastic surface, conditioning the coil or spool feed filament at an elevated temperature whilst under axial tension so as to reduce coil or spool memory in the filament, and injection moulding a thermoplastic pull through profile about at least one axial zone of said filament, said injection moulding being with a molten thermoplastic capable of "keying" to the surface of the monofilament at a temperature below the melting point of the filament.

In another aspect the present invention consists in a pull through useably as an endoscope cleaning apparatus said apparatus comprising or including an elongate member capable of being inserted in part through a conduit (e.g. an endoscope) and thereafter to be pulled fully therethrough, said elongate member being at least in part of a first plastics material or first plastics materials (hereafter "first plastics material"), and an injection moulded form carried at and/or adjacent one end of said elongate member, said form being of a second plastics material or second plastics materials (hereafter "second plastics material") and being such as to provide a smoothing and/or cleaning effect upon its pull through of the conduit (e.g. an endoscope) of appropriate configuration and/or dimension, wherein the form of said second plastics material has been injection moulded onto said first plastics material of said elongate member, the melting point of said second plastics material being less than that of said first plastics material.

As used herein "melting point" in respect of the first plastics material and/or second plastics material includes melting of the material or, if a blend, melting of sufficient material thereof.

Preferably said elongate member is preferably a string like member.

Preferably said elongate member is at least substantially formed of a suitable plastics material.

Preferably said suitable plastics material is at least 50% PP (polypropylene).

Preferably said elongate member is a monofilament.

Preferably said monofilament is 100% PP albeit (optionally blown by a blowing agent thereby to assume a better roundness in cross-section).

Optionally said suitable plastics material for the elongate member is 50% HDPE and 50% PP by weight as a blend or a coaxial make up of a single monofilament).

Preferably said injection moulded form is of a thermoplastic material having a melting point less than that of the first plastics material or the material providing at least the axial strength region of said elongate member.

Preferably the two plastics material are such as to enable some degree of melding, the melting point differential between the two plastics materials lending themselves to that outcome.

Preferably the second plastics material in an elastomer with LLDPE.

In another aspect the present invention consists in endoscope cleaning apparatus substantially as hereinafter described with reference to the accompanying drawings.

In still a further aspect the present invention consists in a method of manufacturing endoscope cleaning apparatus in accordance with the present invention which comprises or includes taking or providing an elongate member as aforesaid and thereafter injection moulding on or adjacent (or both) one end thereof said injection moulded form, said injection moulded form being of a second plastics material of lower melting point than the plastics material of that region (at least) of said elongate member on which the moulded form is injected.

In another aspect the present invention consists in endoscope cleaning apparatus prepared by a method in accordance with the present invention.

In still a further aspect the present invention consists in use of apparatus in accordance with the present invention to clean an endoscope or endoscopes.

BRIEF DESCRIPTION OF THE DRAWINGS

Preferred form of the present invention will now be described with reference to the accompanying drawings in which.

DETAILED DESCRIPTION OF THE PREFERRED EMBODIMENTS

Figure 1:
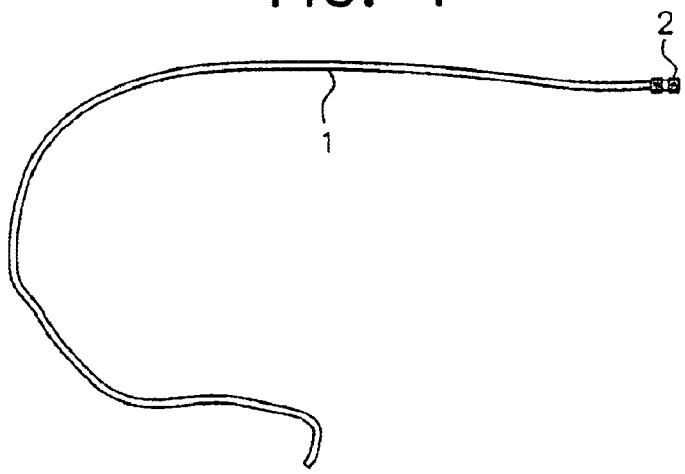
FIG. 1 is a reduced view of a preferred form of the present invention having an injection moulded form of said second plastics material at the end of a pull through type filament of said first plastics material, said pull through elongate member being preferably flexible and being able to pull the brush like form of the injection moulded form to achieve a cleaning effect in an appropriately dimensioned endoscope.

In the preferred form of the present invention the pull through is a cut to length straight and threadable monofilament of a suitable polypropylene. Preferably a tempered extruded polypropylene (eg; homopolymer P.P. supplied by Fina Chemicals, Europe or Honam Petrochemical, Korea) that has a $CO_2$ blown section (as a result of there having been foaming agents included with the polypropylene at the extrusion stage thereof) provides the monofilament, such monofilament assuming a substantially round cross section. Whilst coaxially different materials may be used that is not a preferred option and nor is blended material owing to delamination. Delamination problems may be overcome by better compounding prior to extrusion.

PP monofilament produced on single screw extruder 5 zones reverse temperature profile.

Polymer Base—Polypropylene homopolymer MFI3.5

Additives—Hydrocerol foaming agent let down into LDPE base.

Colour fluoro red let down into LLDPE base/Food contact safe.

Processing Data

Polymer and additives are pre-mixed. Additive percentages are precise.

Processing through the extruder using the correct temperature allows a controlled Carbon Dioxide release in the centre of the extrudate when extruded through the nozzle and exposed to the pressure drop in the atmosphere for a short time before being quenched, extrudate is drawn away from the die nozzle at a precise constant speed before being reheated in hot air.

Once the extrudate has been reheated it is then pulled down many times faster than the extrusion speed thus forming molecular chains which results in the extrudate becoming strong in the longitudinal direction. In doing this, lateral strength is extensively reduced and the extrudate remains stressed. The surface of the extrudate is then heat treated under tension to biaxially orientate the surface molecules of the extrudate before being precision cross wound to a diameter of 130 mm approx on a PVC core. The product is shrink wrapped for transportation and hygiene purposes.

The most preferred plastics material is a homopolymer polypropylene supplied by Finapro Chemicals or Honan.

That product with an inclusion of hydrocerol $CO_2$ is extruded to provide a monofilament of density about 0.97. Extruded PP filament tempered at about 130° C. is 0.9 mm (±5%) in diameter.

Conditioning

Because the extrudate is packaged hot and stressed, it takes on a very acute memory. Annealing or reheating the extrudate below a temperature less than the softening point of the polymer under light tension allows the molecules in the extrudate to relax thus eliminating the memory. A consequence of such conditioning is that the product will shrink.

The pre-conditioning tunnel is a simple heat tunnel during which the monofilament is drawn under some degree of tension (preferably from 91 to 95° C. (most preferably 93 to 95° C.) for about 12 seconds) so as to achieve an axial extension of no greater than 5% but preferably more than 1% during such conditioning).

The monofilament itself has a pull through head profile of a suitable material injection moulded there around at a temperature not sufficient to melt the monofilament (at least in total) at that point (or those points) and preferably not at all.

Whilst ideally the surface of the polypropylene monofilament has been pre-conditioned at an elevated temperature in order to take away the memory of its spool or coil supply, such preconditioning temperature is sufficient only to soften the outer surface to ensure better keying with the material and not to detract from the prior higher temperature tempering of the monofilament to prevent "fluffiness".

Figure 4:
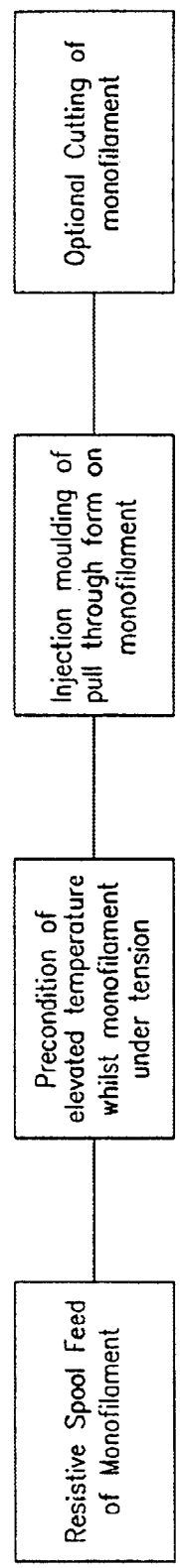
FIG. 4 shows a preferred manufacturing sequence.

In the preferred form of the present invention the arrangement is as shown in FIG. 4 where the injection moulding is performed using any appropriate injection moulding machine (for example, a BOY™ 22AVV) and a cassette or other off take of the output product bundles.

In another embodiment of the present invention (much less preferred as less easily threaded and more prone to delamination) the elongate injection molded form 2 may be of a suitable plastics material (such as 50% HDPE and 50% P.E.). Such a HDPE/PP blend has when formed and stretched a uniaxial orientation and at that end of the filament material 1 onto which the injection molded form 2 is injection molded there is a material melting point greater than that of the injection molded form material.

The injection moulded form 2 however is of a thermoplastic capable of being injection moulded. Such materials include a combination of an elastomer and LLDPE and preferably have a melting point below that of the material 1 so as to not destroy the structure of the filament 1 and thus the integrity of the composite device.

In the preferred form of the present invention therefore preferably the monofilament is either a polypropylene or a polypropylene/high density polyethylene mix. The head is preferably a linear low density polyethylene/elastomer mix but alternative could be of elastomer alone, high density polyethylene alone or TPR.

The pull throughs thus made can have the pull through profile of any appropriate form but preferably one that is symmetric about the monofilament into which it is keyed.

Figure 2:
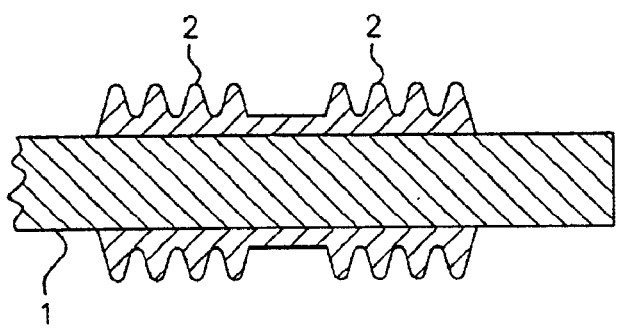
FIG. 2 is a cross section along the longitudinal axis of the injection moulded form end of the cleaning apparatus of FIG. 1, FIG. 3A, 3B and C show some alternatives to the embodiment of FIG. 2.
Figure 3A:
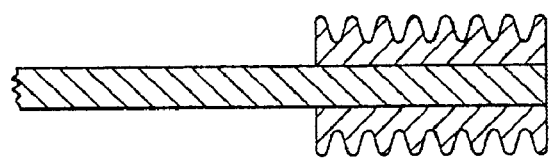
Figure 3B:
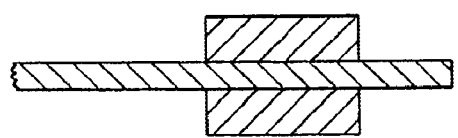
Figure 3C:
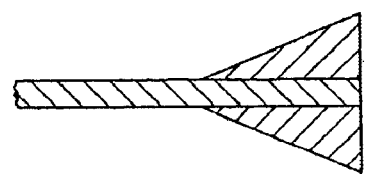

To assist such moulded symmetry of the pull through head preferably the waisted region of the filament (see FIG. 2) is support on a pin or the like member in the mould cavity.

Whilst annular flutes or the like can be provided these need not necessarily be present. Moreover for purposes other than endoscope cleaning or smoothing purposes other forms (brush-like or not) can be prepared.

A person skilled in the art will appreciate how (as shown) injection moulded form 2 can be brush like in character (whether having continuous or discontinuous annular ridges or the like being provided to exert a cleaning or smoothing effect).

The dimensions will be as varied as are the dimensions (diameter and length) of, for example, endoscopes.

For usual endoscope purposes an ideal length of a pull through is from 30 to 220 cm with the pull through profile being of a circular cross-section at its maximum dimension with such diameter being in the range of from 0.95 to 4.5 mm.

Other uses to which such pull throughs can be put include the cleaning of fuel lines, the cleaning of firearms, etc.

In use the pull through filament 1 would be inserted into the conduit to be pulled through (e.g. an endoscope, a fuel line, etc.) and thereafter the injection molded form 2 would be pulled through using the filament material 1.

What is claimed is:

1. A pull through comprising
   a filament having at least a thermoplastics surface, and
   a molded thermoplastic mass about said filament defining a pull through profile adapted for the purpose of the pull through,
   the filament being a monofilament sufficiently stiff at ambient temperature to enable threading of the filament through a passageway of a member,
   and said molded thermoplastic mass being of a material of a lower melting point than at least part of said filament.

2. The pull through of claim 1, wherein said monofilament is of a single plastic material.

3. The pull through of claim 2, wherein said single plastic material is polypropylene.

4. The pull through of claim 1, wherein the molded thermoplastic mass is of polyethylene and a polyolefin elastomer.

5. The pull through of claim 1, wherein said filament is round in section.

6. The pull through of claim 1, wherein said molded thermoplastic mass is adjacent one end of said filament.

7. The pull through of claim 1, wherein said filament lies substantially straight and is substantially free of any spool or coil memory of spooling or coiling previous to the mass being molded thereon.

8. The pull through of claim 1, wherein said molded thermoplastic mass has been injection molded said filament only once the thermoplastic surface of said filament onto which said filament is injection molded has been at least one of softened and conditioned.

9. The pull through of claim 8, wherein said filament is a monofilament of polypropylene that has been heated to a range between 91 and 95° C.

10. The pull through of claim 9, wherein said heating is for a period of 8 to 15 seconds.

11. The pull through of claim 10, wherein said polypropylene monofilament is extruded while exposed to a gas generating agent which will expand a core region thereof upon die emergence.

12. The pull through of claim 11, wherein said gas generating agent releases $CO_2$.

13. The pull through of claim 8, wherein said heating is to a range between 91 to 95° C. for 8 to 15 seconds.

14. The pull through of claim 11, wherein said gas generating agent inclusion enhances a circularity of cross-section of the monofilament from the extrusion die.

15. The pull through of claim 1, wherein said filament has been conditioned by heating and stretching prior to said mass being injection molded.

16. The pull through of claim 15, wherein said filament has been stretched axially from 1 to 5% of its length from a feeder spool or coil.

17. The pull through of claim 1, wherein said mass is of a profile that is laterally symmetric about said filament.

18. A pull through endoscope cleaning apparatus, said apparatus comprising
   an elongate member capable of being inserted in part through a conduit and thereafter to be pulled fully therethrough, said elongate member being at least in part a first plastic material, and
   an injection molded form located at least adjacent to one end of said elongate member, said form being of a second plastic material and providing at least one of a smoothing and a cleaning effect upon being pulled through the conduit,
   the form of said second plastic material being injection molded onto said first plastic material of said elongate member, a melting point of said second plastic material being less than that of said first plastic material.

19. The pull through of claim 18, wherein prior to the molding of the injection molded form there is a heating of the elongate member.

20. The pull through of claim 19, wherein said elongate member is a string member.

21. The pull through of claim 19, wherein said elongate member is at least substantially formed of said first plastic material.

22. The pull through of claim 21, wherein said first plastic material is at least 50% polypropylene.

23. The pull through of claim 18, wherein said elongate member is a monofilament.

24. The pull through of claim 23, wherein said monofilament is 100% polypropylene.

25. The pull through of claim 23, wherein said first plastic material for the elongate member is about 50% HDPE and about 50% polypropylene by weight as a blend.

26. The pull through of claim 18, wherein the two plastic materials enable a degree of melting.

27. The pull through of claim 18, wherein the second plastic material is an elastomer with LLDPE.

* * * * *